United States Patent
Koch et al.

(10) Patent No.: US 7,426,867 B2
(45) Date of Patent: Sep. 23, 2008

(54) ELECTROMAGNETIC ACOUSTIC TRANSDUCERS FOR USE IN ULTRASOUND INSPECTION SYSTEMS

(75) Inventors: Roman Heinrich Koch, Bayern (DE); Andrew May, Schenectady, NY (US); Jian Li, Schenectady, NY (US)

(73) Assignees: General Electric Company, Niskayuna, NY (US); GE Inspection Technologies, GmbH, Huerth (DE)

( * ) Notice: Subject to any disclaimer, the term of this patent is extended or adjusted under 35 U.S.C. 154(b) by 411 days.

(21) Appl. No.: 11/240,056

(22) Filed: Sep. 30, 2005

(65) Prior Publication Data
US 2007/0074572 A1  Apr. 5, 2007

(51) Int. Cl.
*G01N 9/24* (2006.01)
*G01N 27/72* (2006.01)

(52) U.S. Cl. .......................... 73/627; 73/622; 324/226; 324/227

(58) Field of Classification Search ............... 73/627, 73/643, 642, 644, 622, 635, 636, 637, 638, 73/639; 367/140, 168; 324/226, 227
See application file for complete search history.

(56) References Cited

U.S. PATENT DOCUMENTS

| | | | | |
|---|---|---|---|---|
| 2,912,523 A * | 11/1959 | Knowles et al. | ............. | 381/418 |
| 4,104,922 A * | 8/1978 | Alers et al. | ................... | 73/643 |
| 4,449,411 A * | 5/1984 | Suhr et al. | ................... | 73/643 |
| 4,691,572 A * | 9/1987 | van den Berg et al. | ........ | 73/643 |
| 4,777,824 A | 10/1988 | Alers et al. | | |
| 5,721,379 A | 2/1998 | Palmer et al. | | |
| 5,837,898 A | 11/1998 | MacLauchlan | | |
| 6,009,756 A | 1/2000 | Willems et al. | | |
| 6,125,703 A * | 10/2000 | Mac Lauchlan et al. | ........ | 73/592 |
| 6,125,706 A * | 10/2000 | Buttram et al. | ............... | 73/643 |
| 6,176,132 B1 * | 1/2001 | MacLauchlan | ............ | 73/290 V |
| 6,250,163 B1 * | 6/2001 | MacLauchlan et al. | ........ | 73/643 |
| 6,282,964 B1 * | 9/2001 | Hancock et al. | ............... | 73/622 |
| 6,561,035 B2 | 5/2003 | Passarelli, Jr. | | |
| 6,839,640 B2 * | 1/2005 | Ohtani | ........................ | 702/35 |
| 6,920,792 B2 * | 7/2005 | Flora et al. | .................... | 73/622 |
| 7,165,453 B2 * | 1/2007 | Flora et al. | .................... | 73/643 |
| 2003/0159516 A1 | 8/2003 | Hubschen | | |
| 2005/0120803 A1 | 6/2005 | Sokol et al. | | |
| 2007/0230737 A1 * | 10/2007 | Hyde | ........................ | 381/421 |

FOREIGN PATENT DOCUMENTS

DE     19549207 C2    10/1997
WO     WO 02/04135 A1  1/2002

* cited by examiner

*Primary Examiner*—Hezron E. Williams
*Assistant Examiner*—Jacques M. Saint-Surin
(74) *Attorney, Agent, or Firm*—Penny A. Clarke

(57) ABSTRACT

An ultrasound system for inspecting an object is provided. The ultrasound system includes an electromagnetic acoustic transducer (EMAT) and a pulser-receiver system. The EMAT is configured to generate acoustic signals representative of the area being inspected and comprises a flux concentrating non-conductive pole piece separating a radio frequency (RF) coil and a magnet. The pulser-receiver system is coupled to the EMAT and configured to receive the acoustic signals and convert the acoustic signal to electrical signals.

16 Claims, 3 Drawing Sheets

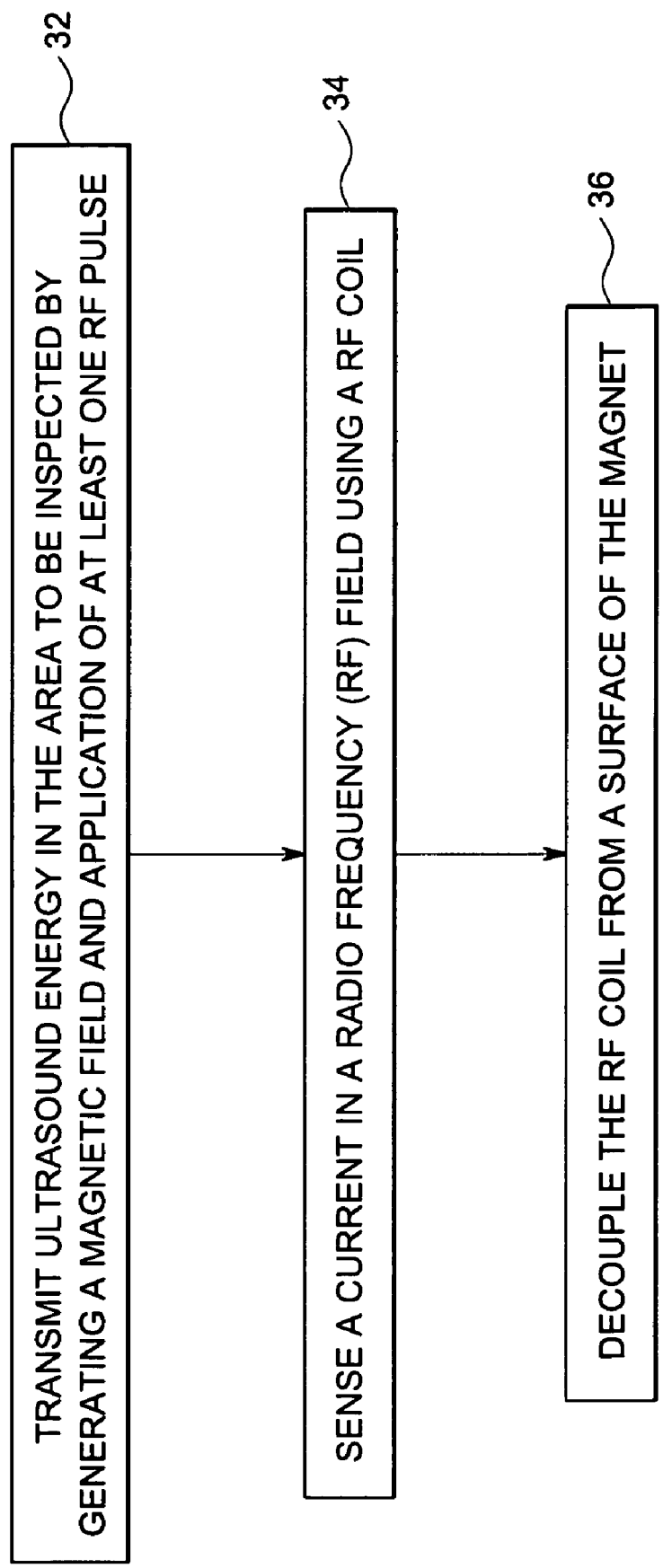

ELECTROMAGNETIC ACOUSTIC TRANSDUCERS FOR USE IN ULTRASOUND INSPECTION SYSTEMS

BACKGROUND

The invention relates generally to inspection systems and more specifically to electromagnetic acoustic transducers for use in ultrasound systems.

Ultrasonic inspection is a commonly used non-destructive evaluation (NDE) technique for detecting corrosion and cracking in different objects such as metallic components, pipes, etc. Electromagnetic acoustic transducers (EMATs) are ultrasonic transducers that couple acoustic energy into and out of an object electromagnetically rather than through the use of an acoustic coupling medium such as water.

An EMAT generates ultrasonic energy in a conductive sample under test as follows. A magnetic field is applied to the sample using a magnet, and radio frequency (RF) eddy-currents are induced into the sample using a RF coil. The RF pulse interacts with the magnetic field to produce a mechanical force, which in turn produces ultrasonic waves at the radio frequency.

The absence of a coupling medium enables EMAT transducers to be used in a variety of applications where the use of the coupling medium between the transducer and the specimen is either impractical or undesirable. For example, if the specimen is coated with an acoustically attenuating material, acoustic wave propagation is not feasible. The absence of the coupling medium also improves reliability of the scanning process and hence reduces the risk of having to perform re-inspections in cases where the coupling medium has been lost. The use of EMATs enables inspection at elevated temperatures, on moving objects, in vacuum or oily or rough surfaces and also in remote locations.

EMATs typically have greatly reduced transduction efficiency compared with acoustically coupled transducers. Thus, they are not generally adaptable for use with existing ultrasonic inspection equipment such as ultrasound (UT) pulser-receivers or flaw detectors. Typically, equipment manufacturers design custom EMAT driver/receiver electronics using high-power tone-burst generators. However, these systems typically generate low-bandwidth signals compared to conventional UT pulser-receivers, which limit inspection resolution.

Most EMATs generally include a magnet and a radio frequency (RF) coil that are arranged in close proximity with each other. Such an arrangement causes parasitic eddy currents to be induced in the magnet thus causing the RF field to cancel out rapidly when the EMAT is lifted off from the object's surface thus reducing the lift-off performance of the probe. The close proximity of the RF coil and the magnet also decreases the transduction efficiency of the transducer.

Thus, there is a need for designing an electromagnetic transducer that is capable of being used with existing ultrasound receiver systems and which also has improved transduction efficiency and lift-off performance.

BRIEF DESCRIPTION

Briefly, according to one embodiment of the invention, an ultrasound system for inspecting an object is provided. The ultrasound system includes an electromagnetic acoustic transducer (EMAT) configured to generate acoustic signals representative of the area being inspected. The EMAT includes a flux concentrating non-conductive pole piece and a radio frequency (RF) coil adapted to transmit an RF field and to receive signals representative of the area being inspected. The EMAT further includes a magnet for generating a static magnetic field. The pole piece separates the RF coil from the magnet. The ultrasound system further includes a pulser-receiver system coupled to the EMAT and configured to receive the acoustic signals and convert the acoustic signal to electrical signals.

In another embodiment of the invention, a method for inspecting an area of an object using an electromagnetic acoustic transducer (EMAT) is provided. The method includes transmitting ultrasound in the area to be inspected by generating a magnetic field and applying at least one radio frequency (RF) pulse to the object. The magnetic field is generated using a magnet. The method further includes sensing a change in a radio frequency (RF) field using the RF coil. The method further includes decoupling the RF coil from a surface of the magnet.

DRAWINGS

These and other features, aspects, and advantages of the present invention will become better understood when the following detailed description is read with reference to the accompanying drawings in which like characters represent like parts throughout the drawings, wherein:

FIG. 3 is a flow chart describing one technique for inspecting an object using an electromagnetic acoustic transducer.

DETAILED DESCRIPTION

Figure 1:
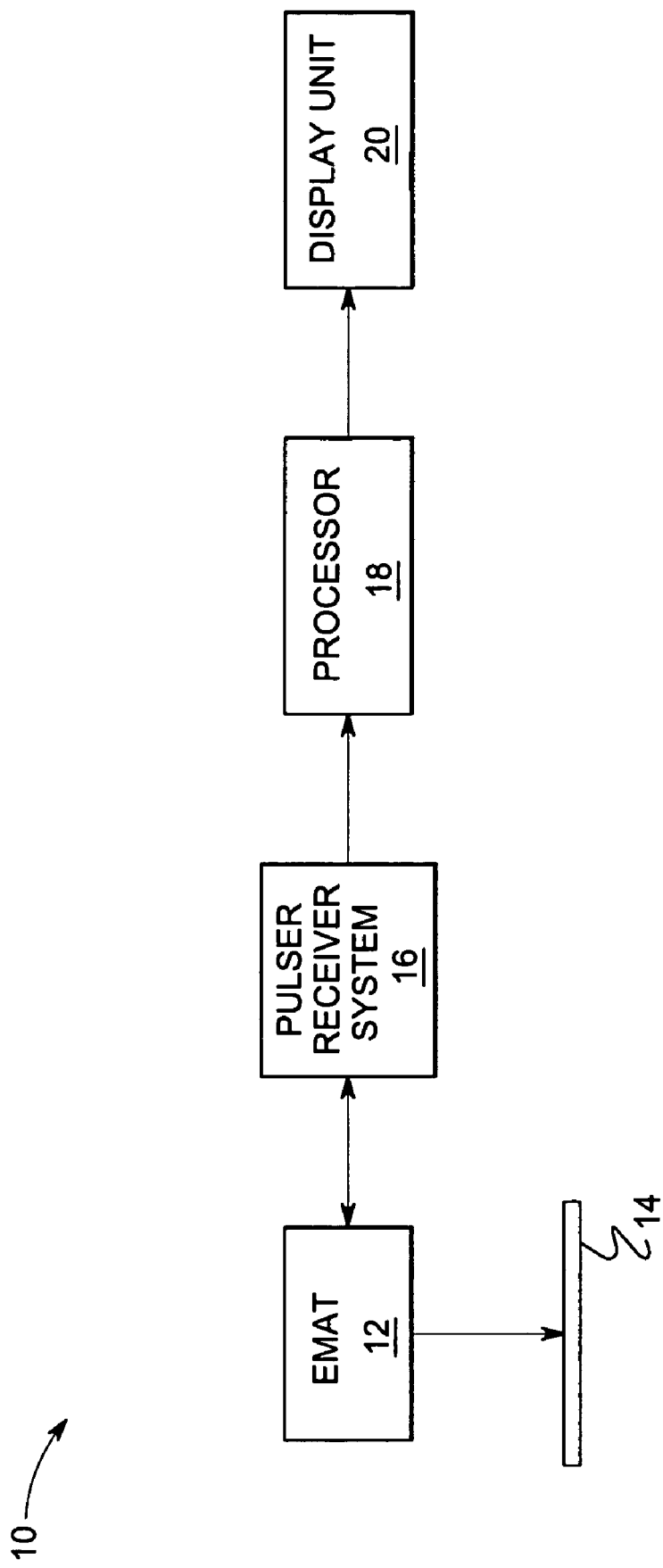
FIG. 1 is a schematic diagram of an exemplary inspection system implementing an electromagnetic acoustic transducer (EMAT) according to one aspect of the invention.

FIG. 1 is a block diagram of one embodiment of an ultrasound inspection system used to inspect an object. The ultrasound inspection system 10 implements an electromagnetic acoustic transducer (EMAT) in conjunction with a pulser receiver system to inspect the object. Each block is explained in further detail below.

As used herein, "adapted to", "configured" and the like refer to devices in a system to allow the elements of the system to cooperate to provide a described effect; these terms also refer to operation capabilities of electrical or optical elements such as analog or digital computers or application specific devices (such as an application specific integrated circuit (ASIC)), amplifiers or the like that are programmed to provide an output in response to given input signals, and to mechanical devices for optically or electrically coupling components together.

Electromagnetic acoustic transducer (EMAT) 12 is configured to generate acoustic signals representative of an area being inspected on object 14. The EMAT comprises a flux concentrating non-conductive pole piece, a radio frequency coil and a magnet. The structure and operation of the EMAT will be described in further detail with reference to FIG. 2.

Continuing with FIG. 1, the ultrasound inspection system further comprises a pulser-receiver system 16 coupled to the electromagnetic acoustic transducer 12. The pulser receiver system is configured to receive the acoustic signals that are representative of the area of the object being inspected. The receiver system converts the acoustic signal to electrical signals for further processing by processor 18. In one embodiment, the pulser receiver system comprises an ultrasound receiver system. More particularly, the pulser receiver system is configured to excite a coil 30 of EMAT 12 by supplying radio frequency pulses to the coil 30. Exemplary pulses include spike pulses and square wave pulses.

Processor 18 receives the electrical signals generated by pulser receiver system 16. The processor may apply various signal processing algorithms on the received data to generate required information such on flaws, cracks, etc. on the object being inspected. The processor may also be configured to generate an image of the object and display the processed data along with the object on display unit 20.

Figure 2:
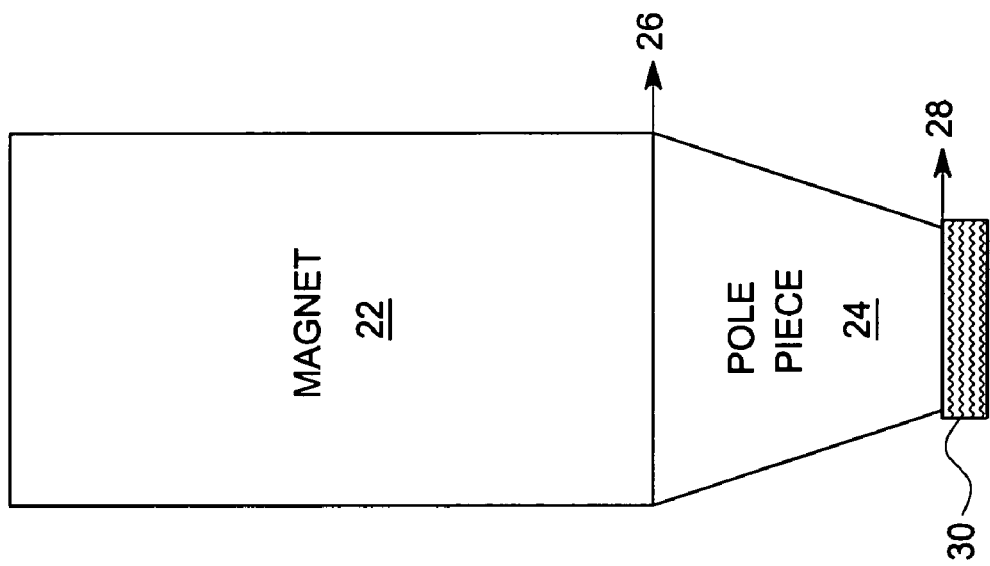
FIG. 2 is a cross-sectional view of an electromagnetic acoustic transducer implemented in accordance with one aspect of the invention.

FIG. 2 is a cross-sectional view of an electromagnetic acoustic transducer (EMAT) for implementation with the ultrasound inspection system described in FIG. 1. The EMAT includes a magnet 22, a pole piece 24 and a radio frequency coil 30. Each block is described in further detail below.

Magnet 22 is configured for generating a static magnetic field. As is well known to one skilled in the art, the magnetic field is required for efficient generation of ultrasound via the Lorentz force or magnetostriction mechanisms. In particular embodiments, magnet 22 may comprise a permanent magnet or periodic permanent magnets.

Radio frequency (RF) coil 30 is configured to generate a radio frequency field around the area being inspected by the EMAT. The electric current induced by the radio frequency coil interacts with the magnetic field generated by the magnet 22 and causes the Lorentz force. In one embodiment, the RF coil is configured to transmit the RF field and receive the electrical signals that are representative of the area being inspected.

In one embodiment, the RF coil 30 comprises a spiral pancake coil. The spiral pancake coil may be formed, for example, of at least one of copper wires, ferromagnetic wires or printed circuit coils. In one embodiment, the spiral pancake coil is disposed on a ceramic substance. In another embodiment, the spiral pancake coil is formed on a polymer substrate.

Flux concentrating non-conductive pole piece 24 is configured to focus the static field generated by magnet 22 to the area being inspected on object 14. The pole piece comprises a top surface 26 and a bottom surface 28. The bottom surface may define various shapes such as an ellipse, a circle, a rectangle or a square, etc.

The pole piece is tapered such that an area of the bottom surface is less than an area of the top surface as shown in FIG. 2. The tapering of the pole piece increases the transduction efficiency, as the static magnetic field is concentrated in a small area under the pole. The tapered pole piece design also lends itself to the generation of polarized shear-wave acoustic waves.

In one embodiment, pole piece 24 is non-uniformly tapered. The non-uniform tapering of the pole piece causes the generation of a static magnetic field pattern that is longer in one direction. Such patterns can be used to generate linearly polarized shear waves.

The pole piece comprises a material that is electrically non-conductive. This property of the pole piece decouples the RF coil 30 from the conducting surface of magnet 22 thus reducing the formation of parasitic eddy currents. The reduction of induced eddy currents in the magnet results in substantial reduction of acoustic and mechanical vibrations of the magnet. Another advantage of the reduction of induced eddy current is the corresponding increase in the transduction efficiency. The reduction of eddy currents on the magnet also greatly decreases the decay rate of the net RF field with liftoff from the sample.

In one embodiment, the thickness of the magnet 22 is greater than a thickness of the flux concentrating non-conductive pole piece 24. In a further embodiment, the thickness of the magnet is between three to six times greater than the thickness of the flux concentrator. In one specific embodiment, the thickness of the magnet is five times greater than the thickness of the flux concentrator.

The electromagnetic acoustic transducer described above has many advantages including minimized clamping forces and sliding friction when used on ferromagnetic objects. The electromagnetic acoustic transducer described above is compatible with existing ultrasound pulser receiver and flaw detector systems that are typically used with piezoelectric transducers.

FIG. 3 is a flow chart describing one method to inspect an object using an electromagnetic acoustic transducer coupled to a pulser receiver system. The pulser receiver system may include an ultrasound receiver system. Each step in the flow chart is described in further detail below.

In step 32, ultrasound energy is transmitted into an area to be inspected by generating a magnetic field and application of at least one RF pulse. The magnetic field is generated by a permanent magnet such as the one described in FIG. 2.

In step 34, a current is sensed in a radio frequency (RF) field. The radio frequency field is generated using a radio frequency (RF) coil such as the one described in FIG. 2.

In step 36, the RF coil is decoupled from a conducting surface of the magnet. The decoupling is achieved by using a flux-concentrated, non-conductive pole piece. The decoupling of the RF coil from the magnet increases the transduction efficiency. In one embodiment, the transduction efficiency is about 10%.

The above-described technique provides various advantages such improved signal to noise ratio and large bandwidth and resolution. In one embodiment, the signal to noise ratio achieved using the above technique is about 30 dB. In addition, the technique requires lower power requirements. In one embodiment, the power required by an inspection system employing the technique described in FIG. 3 is about one tenth the power requirements of a conventional ultrasound inspection system.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An ultrasound system for inspecting an object, the ultrasound system comprising:
    an electromagnetic acoustic transducer (EMAT) configured to generate acoustic signals representative of the area being inspected, wherein the EMAT comprises:
        a flux concentrating non-conductive pole piece, wherein the pole piece comprises a top surface and a bottom surface, and wherein the pole piece is tapered such that an area of the bottom surface is less than an area of the top surface;
        a radio frequency (RF) coil configured to transmit an RF field and to receive signals representative of the area being inspected;
        a magnet for generating a static magnetic field, wherein the pole piece separates the RF coil from the magnet; and
    a pulser-receiver system coupled to the EMAT and configured to receive the acoustic signals and convert the acoustic signal to electrical signals.

2. The ultrasound system of claim 1, wherein the bottom surface defines at least one of an ellipse, a circle, a rectangle or a square.

3. The ultrasound system of claim 1, wherein the pole piece is non-uniformly tapered.

4. The ultrasound system of claim 1, wherein the pole piece is electrically non-conductive and magnetic.

5. The ultrasound system of claim 4, wherein the pole piece is ferromagnetic.

6. The ultrasound system of claim 1, wherein the pulser receiver system comprises an ultrasound receiver system.

7. The ultrasound system of claim 6, wherein the RF coil comprises a spiral pancake coil.

8. An ultrasound system for inspecting an object, the ultrasound system comprising:
    an electromagnetic acoustic transducer (EMAT) configured to generate acoustic signals representative of the area being inspected, wherein the EMAT comprises:
        a flux concentrating non-conductive pole piece,
            a radio frequency (RF) coil configured to transmit an RF field and to receive signals representative of the area being inspected, and
            a magnet for generating a static magnetic field, wherein the pole piece separates the RF coil from the magnet; and
    a pulser-receiver system coupled to the EMAT and configured to receive the acoustic signals and convert the acoustic signal to electrical signals, wherein a thickness of the magnet is greater than a thickness of the flux concentrator.

9. A method for inspecting an area of an object using an electromagnetic acoustic transducer (EMAT), the method comprising:
    transmitting ultrasound energy in the area to be inspected by generating a magnetic field and applying at least one radio frequency (RF) pulse to the object, wherein the magnetic field is generated using a magnet;
    sensing a current in a radio frequency (RF) field using the RF coil;
    decoupling the RF coil from a surface of the magnet, wherein the step of decoupling is achieved using a flux-concentrated, non-conductive pole piece; and
    tapering the pole piece to concentrate the magnetic field on the area to be inspected.

10. The method of claim 9, wherein the pole piece is non-uniformly tapered.

11. The method of claim 9, wherein the transmitting step comprises generating at least one polarized shear-wave accoustic mode in the object under inspection.

12. The method of claim 9, wherein the transmitting step comprises generating at least one linearly polarized shear-wave accoustic mode in the object under inspection.

13. An ultrasound system for inspecting an area of an object, the ultrasound system comprising:
    an electromagnetic acoustic transducer (EMAT) configured to generate acoustic signals representative of the area being inspected wherein the EMAT comprises:
        a flux concentrating non-conductive pole piece, wherein the pole piece comprises a top surface and a bottom surface, and wherein the pole piece is tapered such that an area of the bottom surface is less than an area of the top surface;
        a radio frequency (RF) coil;
        a magnet for generating a static magnetic field, wherein the pole piece separates the RF coil from the magnet; and
    an ultrasound receiver system coupled to the EMAT and configured excite the RF coil and to receive the acoustic signals and convert the acoustic signal to electrical signals.

14. The ultrasound system of claim 13, wherein the pole piece is electrically non-conductive and magnetic.

15. The ultrasound system of claim 13, wherein the RF coil is configured to transmit a RF field and receive signals representative of the area being inspected.

16. An electromagnetic acoustic transducer (EMAT) comprising:
    a flux concentrating pole piece, wherein the pole piece is electrically non-conductive and magnetic, wherein the pole piece comprises a top surface and a bottom surface, and wherein the pole piece is tapered such that an area of the bottom surface is less than an area of the top surface;
    a radio frequency (RF) coil configured to transmit a RF field and to receive signals representative of the area being inspected; and
    a magnet for generating a static magnetic field, wherein the pole piece separates the RF coil from the magnet.

* * * * *